United States Patent [19]
Kai

[11] Patent Number: 4,825,934
[45] Date of Patent: May 2, 1989

[54] CUSHIONING SHEET FOR USE IN DENTURE CASTING

[76] Inventor: Satoshi Kai, 1-56, Meguri 1-chome, Hirakata-shi, Osaka, Japan

[21] Appl. No.: 108,289

[22] Filed: Oct. 14, 1987

[30] Foreign Application Priority Data

Oct. 16, 1986 [JP] Japan ................................ 61-159916

[51] Int. Cl.$^4$ ................................................. B22C 9/04
[52] U.S. Cl. ...................................... 164/361; 164/35; 164/246; 164/DIG. 4; 249/54; 249/62
[58] Field of Search .................. 164/246, 45, 34, 35, 164/36, 361, DIG 4, DIG. 15; 249/61, 62, 54

[56] References Cited

U.S. PATENT DOCUMENTS

| | | | |
|---|---|---|---|
| 4,356,859 | 11/1982 | Savage | 164/246 |
| 4,531,566 | 7/1985 | Boettcher | 164/246 |
| 4,573,921 | 3/1986 | Berger | 249/62 |

FOREIGN PATENT DOCUMENTS 153283 1/1956 Sweden ................................ 164/34

Primary Examiner—Richard K. Seidel
Attorney, Agent, or Firm—Wenderoth, Lind & Ponack

[57] ABSTRACT

A cushioning sheet made of a flammable material for use, e.g. in denture casting. It is inserted into a casting frame and adapted to burn out when heated to leave a space between a casting frame and a casting mold in the frame. The space serves to absorb the difference in the thermal expansion between the frame and the mold, thus preventing the casting mold from cracking or breaking. The cushioning sheet is formed with apertures. The casting material penetrates through the apertures, abutting against the casting frame to support the casting mold upon the frame even after the cushioning sheet has burnt out.

5 Claims, 2 Drawing Sheets

CUSHIONING SHEET FOR USE IN DENTURE CASTING

BACKGROUND OF THE INVENTION

The present invention relates to a cushioning sheet for use in the casting of a denture or the like. The material serves to absorb the difference in the thermal expansion between a casting frame and a casting material.

FIG. 6 shows, as an example, how a denture is cast in the prior art. A casting mold b in which is embedded a denture model a made of wax (including a denture core) is heated so that the model a will be burnt and flown away, and a molten metal is cast in the space formed by the removal of the model a to form a denture.

If the casting material for forming the casting mold b is not strong enough, it is necessary to fill the casting material into a cylindrical casting frame c as shown in FIGS. 5 and 6 to form a casting mold b. However, the use of the casting frame c poses other problems that the casting mold b might be broken or cracked due to the difference in the thermal expansion between the casting frame c and the casting mold b and that the casting material might partially stick out into the space formed by removing the wax model a. In the former case, the mold will become useless. In the latter case, the resulting denture would not comply with the model in shape. Since a denture is intended to be set in the mouth and brought into occlusion with other teeth, high precision is required.

Therefore, the casting frame c customarily has the whole surface of its inner periphery covered with a cushioning material d made of asbestos to absorb the difference in the thermal expansion. However, since asbestos is so harmful to a human body as to deteriorate the health of persons who inhale its powder, its production cost is soaring.

The dental technicians who handle asbestos are exposed to the danger of inhaling not a small amount of asbestos powder. Thus it has been hoped to develop a cushioning material which substitutes for an asbestos cushion.

SUMMARY OF THE INVENTION

It is an object of the present invention to provide an improved cushioning material which obviates the abovesaid shortcomings.

In accordance with the present invention, there is provided a cushioning sheet for use in the casting of a denture or the like and adapted to cover the entire inner periphery of a casting frame so that a casting material can be poured into the casting frame to form a casting mold and heated to burn off a wax model embedded in the casting mold, a molten metal being cast in a space formed by the removal of the wax model, characterized in that the cushioning sheet is made of a flammable material and formed with a plurality of apertures.

The cushioning material may be synthetic resin such as vinyl chloride and polyethylene, paper, or any other material which burns out at a temperature of 700° to 800° C. The size, number, spacings, and position of the apertures may be determined according to the size of the spaces formed by the burning of the cushioning material, the extent of protrusion of the casting material, the stability of the casting mold, etc.

After covering the entire surface of the inner periphery of the casting frame with the cushioning material of the present invention, the casting material is filled with a wax model into the casting frame and heated to burn and remove the wax model and finally a molten metal is poured into the space formed by the removal of the model to cast a denture or the like in the same manner as in the prior art.

While being heated, the cushioning material is burnt out to leave a space between the casting frame and the casting mold, the space serving to absorb the difference in the thermal expansion therebetween. The casting mold partially protrudes from its surface through the apertures formed in the cushioning material to abut against the casting frame so as to be stopped from falling off the casting frame without hindering the casting of a denture.

If a casting material expanding while hardening is used, the casting frame might crack while hardening since it does not expand. However, since a flammable cushioning material usually has a cushioning action, the expansion of the casting frame is absorbed.

The cushioning material of the present invention can effectively absorb the difference in the thermal expansion between the casting mold and the casting frame, can be produced at a low cost and will not produce a harmful effect on a human body.

BRIEF DESCRIPTION OF THE DRAWINGS

Other features and objects of the present invention will become apparent from the following description taken with reference to the accompanying drawings, in which.

DETAILED DESCRIPTION OF THE PREFERRED EMBODIMENT

Figure 1:
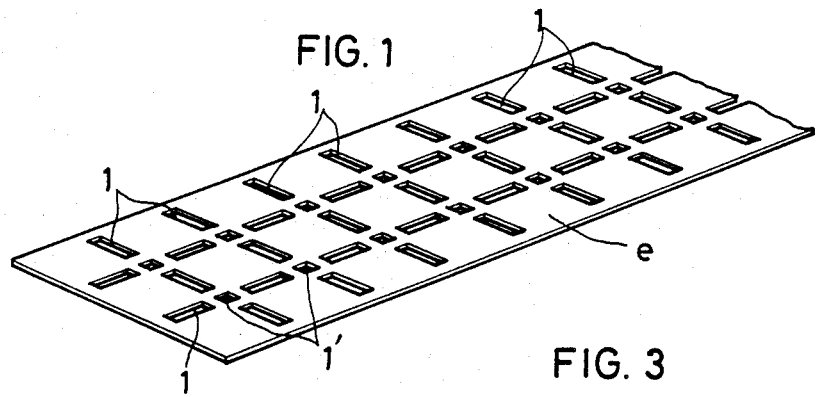
FIG. 1 is a perspective view of an embodiment of the cushioning material in accordance with the present invention.

Referring to the drawings, FIG. 1 shows a preferred embodiment of the present invention in which a cushion is in the form of a sheet e made of expanded vinyl chloride and formed with rectangular apertures 1, 1.5 mm in width $\times 4.5$ mm in length and $1.2 \times 1.2$ mm square apertures 1'. The two kinds of apertures 1, 1' are alternately arranged in a lattice pattern. This cushioning sheet e can be used as a substitute for the prior art asbestos cushion d.

Figure 3:
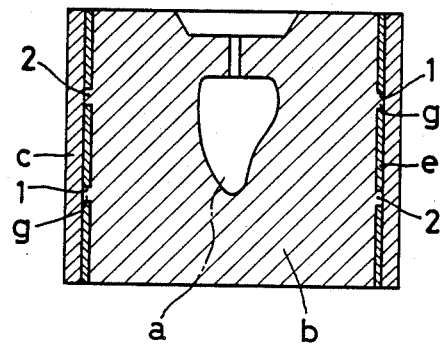
FIGS. 2 to 4 are explanatory views showing how the same is used.
Figure 2:
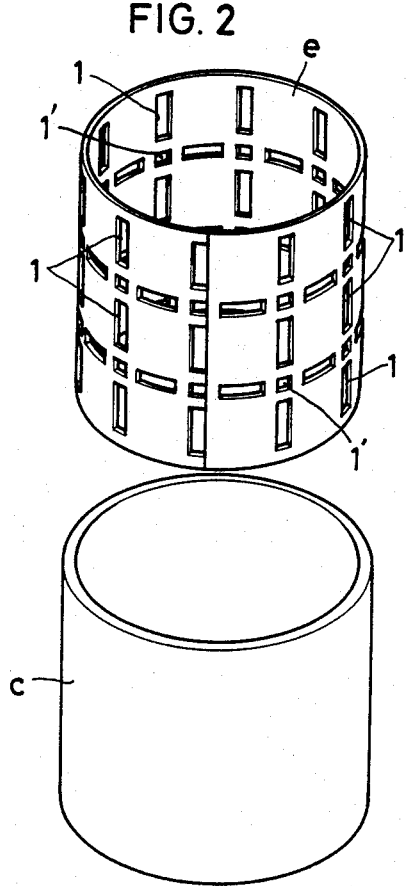
Figure 4:
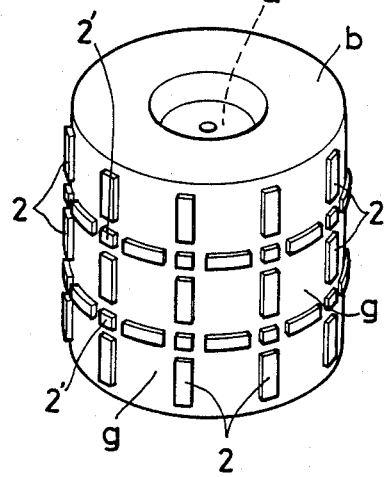
Figure 5:
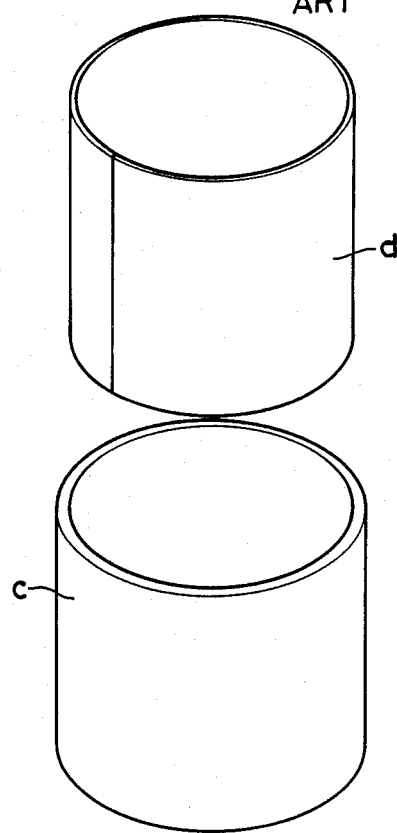
FIGS. 5 and 6 are explanatory views showing how the prior art cushioning material is used.
Figure 6:
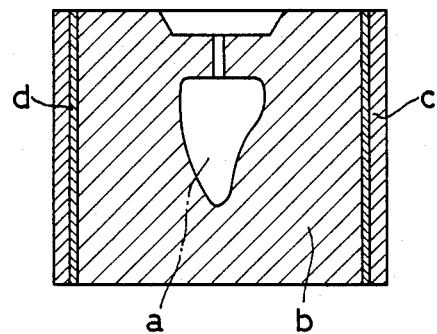

In use, the cushioning sheet e is cut to a length substantially equal to the inner circumference of the casting frame c and rolled into a cylinder as shown in FIG. 2. The rolled cylinder e is then inserted into the casting frame c and the frame is filled with a casting material with a denture model a of wax embedded therein as shown in FIG. 3. The casting material herein used is one made by mixing known embedding materials such as feldspar and silica in a solvent such as water. The casting frame c tilled with the casting material is left as it is to wait for the casting material to harden to some extent. Though the casting material tends to expand while hardening, such expansion will be absorbed by the cushioning action of the cushioning sheet e. If the casting frame has its bottom open, it should be placed on a flat board before filling it with a casting material.

Next the casting frame c is put in an electric furnace and heated to 700° to 800° C. to melt, burn and remove the denture model a. A molten metal is then cast in the space thus formed to form a denture.

While being heated in the furnace, the cushioning sheet e is burnt out to leave a space g between the casting frame c and the casting mold b except the portions where the apertures 1 and 1' were because they are now occupied by the metal. The space g serves to absorb the difference in the thermal expansion between the members c and b, thereby preventing the casting mold b from cracking or breaking. Although the cushioning sheet e is burnt out while heated, the apertures 1 and 1' allow the casting material to partially protrude from its surface to form projections 2 and 2', which abut against the casting frame c, preventing the casting mold b from falling off the casting frame c. Therefore, the presence of the apertures does not hinder the casting in any way.

What is claimed is:

1. In combination, a lost wax casting process casting frame and a cushioning sheet for covering substantially the entire inner periphery of said casting frame used in a lost wax casting process, said cushioning sheet for being placed between a casting material and said casting frame for absorbing both the expansion of the casting material when hardening in said casting frame and the difference in the rates of thermal expansion between the hardened casting material and said casting frame when said casting frame and hardened casting material are heated to burn out said cushioning sheet, said cushioning sheet comprising:

a substantially planar layer of flammable materials;

a plurality of through apertures in said substantially planar layer of flammable material, each one of said plurality of apertures being of a predetermined size relative to the area of said layer of planar material for causing the non-apertured area of said layer of planar material to absorb the force of expansion of the casting material when hardening in said casting frame and to define a space determined by the volume of the non-apertured area to absorb the difference in the rates of thermal expansion between the hardened casting material and said casting frame when said casting frame and the hardened casting material are heated to burn out said layer of planar material, and said predetermined size of said plurality of apertures allowing a portion of the casting material to enter said plurality of apertures and contact said casting frame for forming a sufficient number of predetermined areas of contact between the hardened casting material and said casting frame for retaining the hardened casting material in said casting frame after said layer of casting material has been burned out.

2. A device as in claim 1, wherein said plurality of apertures includes rectangular and square apertures.

3. A device as in claim 2, wherein said plurality of apertures is in a latticed pattern.

4. A device as in claim 3, wherein said flammable layer of planar material burns at 700° to 800° C.

5. A device as in claim 4, wherein said flammable layer of planar material is one of the group consisting of vinyl chloride, polyethylene, and paper.

* * * * *